US009585583B1

(12) United States Patent
Mortara

(10) Patent No.: US 9,585,583 B1
(45) Date of Patent: Mar. 7, 2017

(54) MYOGRAM DETERMINATION FROM ECG SIGNAL

(71) Applicant: Mortara Instrument, Inc., Milwaukee, WI (US)

(72) Inventor: David W. Mortara, Milwaukee, WI (US)

(73) Assignee: MORTARA INSTRUMENT, INC., Milwaukee, WI (US)

( * ) Notice: Subject to any disclaimer, the term of this patent is extended or adjusted under 35 U.S.C. 154(b) by 105 days.

(21) Appl. No.: 14/196,962

(22) Filed: Mar. 4, 2014

(51) Int. Cl.
*A61B 5/0488* (2006.01)
*A61B 5/0402* (2006.01)
(Continued)

(52) U.S. Cl.
CPC ........ *A61B 5/04017* (2013.01); *A61B 5/0205* (2013.01); *A61B 5/0408* (2013.01);
(Continued)

(58) Field of Classification Search
CPC ... A61B 5/0488; A61B 5/0452; A61B 5/0402; A61B 5/0205; A61B 5/04017;
(Continued)

(56) References Cited

U.S. PATENT DOCUMENTS 4,742,831 A  5/1988 Silvian
5,212,476 A  5/1993 Maloney
(Continued)

FOREIGN PATENT DOCUMENTS

WO  WO-2012/106219 A1  8/2012
WO  WO-2013/155196 A2  10/2013

OTHER PUBLICATIONS

Hefftner et al., The electromyogram (EMG) as a control signal for functional neuromuscular stimulation: II Practical demonstration of the EMG signature discrimination system, IEEE Transactions on Biomedical Engineering, 1988, pp. 230-237, vol. 35, Issue 4, IEEE Journals & Magazines, 8 pages.
(Continued)

*Primary Examiner* — Christopher D Koharski
*Assistant Examiner* — Pamela M Bays
(74) *Attorney, Agent, or Firm* — Foley & Lardner LLP

(57) ABSTRACT

Systems and methods for measuring signals representative of muscle activity are provided. One method includes detecting an ECG signal through a plurality of electrodes. The ECG signal includes a plurality of ECG sample signals, and each ECG sample signal is a bipolar signal associated with two of the plurality of electrodes and includes a cardiac signal component and a myographic signal component. The method further includes filtering each of the ECG sample signals to remove at least a portion of the cardiac signal component and generate a combined myographic power signal for the two of the plurality of electrodes with which the ECG sample signal is associated. Each combined myographic power signal represents a myographic potential between the two electrodes. The method further includes calculating individual myographic power signals for each of the plurality of electrodes by applying the combined myographic power signals within a covariance matrix.

14 Claims, 4 Drawing Sheets

(51) Int. Cl.
    *A61B 5/04* (2006.01)
    *A61B 5/0205* (2006.01)
    *A61B 5/0408* (2006.01)
    *A61B 5/0452* (2006.01)
    *A61B 5/0492* (2006.01)
    *A61N 1/37* (2006.01)
    *A61N 1/05* (2006.01)

(52) U.S. Cl.
    CPC .......... *A61B 5/0452* (2013.01); *A61B 5/0488* (2013.01); *A61B 5/0492* (2013.01); *A61B 5/0402* (2013.01); *A61M 2230/005* (2013.01); *A61M 2230/08* (2013.01); *A61N 1/05* (2013.01); *A61N 1/3702* (2013.01)

(58) Field of Classification Search
    CPC ............... A61B 5/0408; A61B 5/0492; A61M 2230/005; A61M 2230/08; A61N 1/3702; A61N 1/05
    USPC .......................................................... 600/510
    See application file for complete search history.

(56) References Cited

U.S. PATENT DOCUMENTS

| | | | |
|---|---|---|---|
| 5,233,999 A | 8/1993 | Dellacorna et al. | |
| 5,505,208 A | 4/1996 | Toomim et al. | |
| 5,513,651 A | 5/1996 | Cusimano et al. | |
| 5,671,752 A | 9/1997 | Sinderby et al. | |
| 5,704,365 A * | 1/1998 | Albrecht | A61B 5/0408 128/901 |
| 5,913,308 A * | 6/1999 | Forbes | A61B 5/0402 600/513 |
| 6,584,347 B1 | 6/2003 | Sinderby | |
| 6,745,062 B1 | 6/2004 | Finneran et al. | |
| 6,813,514 B1 | 11/2004 | Kroll et al. | |
| 6,816,744 B2 | 11/2004 | Garfield et al. | |
| 6,901,286 B1 | 5/2005 | Sinderby et al. | |
| 7,117,035 B2 | 10/2006 | Wagner et al. | |
| 7,158,829 B1 | 1/2007 | Levine | |
| 7,447,542 B2 | 11/2008 | Calderon et al. | |
| 7,457,664 B2 | 11/2008 | Zhang et al. | |
| 7,831,302 B2 | 11/2010 | Thomas | |
| 7,933,643 B1 | 4/2011 | Gill et al. | |
| 8,033,996 B2 | 10/2011 | Behar | |
| 8,200,318 B2 | 6/2012 | Saba et al. | |
| 8,275,451 B2 | 9/2012 | Marossero et al. | |
| 8,332,021 B2 | 12/2012 | Vullings et al. | |
| 8,454,555 B2 | 6/2013 | Struijk et al. | |
| 8,532,774 B1 | 9/2013 | Hedberg et al. | |
| 2007/0225770 A1 | 9/2007 | Lapanashvili | |
| 2008/0287820 A1 | 11/2008 | Ignagni et al. | |
| 2011/0066041 A1 | 3/2011 | Pandia et al. | |
| 2011/0263994 A1 | 10/2011 | Burns et al. | |
| 2013/0171599 A1 | 7/2013 | Bleich et al. | |
| 2013/0213399 A1* | 8/2013 | Hansmann | A61B 5/7203 128/204.23 |

OTHER PUBLICATIONS

Mananas et al., Cardiac Interference in Myographic Signals From Different Respiratory Muscles and Levels of Activity, Papers from 23rd Annual International Conference of the IEEE Engineering in Medicine and Biology Society, Oct. 25-28, 2001; Istanbul, Turkey; 4 pages.

Mintchev, M.P. et al., Reliability of percent distribution of power of the Electrogastrogram in recognizing gastric electrical uncoupling, IEEE Transactions on Biomedical Engineering, 1997, pp. 1288-1291, vol. 44, Issue 12, IEEE Journals & Magazines, 4 pages.

Morabito et al., Neural Network Approaches to the Processing of Experimental Electro-Myographic Data from Non-Invasive Sensors, Applied Computational Electromagnetics Society Journal, Jul. 2003, pp. 76-88, vol. 18, No. 2; Special Issue on Neural Network Applications in Electromagnetics, 14 pages.

Pereira, C.D.M. et al., Development of a two-electrode ECG acquisition system with dynamic interference rejection, Bioengineering (ENBENG), 2011, pp. 1-5, IEEE Conference Publications, 5 pages.

Starc, Vito, Could Determination of Equivalent Dipoles from 12 Lead ECG Help in Detection of Misplaced Electrodes, Computing in Cardiology 2011, pp. 445-448, issue 38, ISBN 0276-6547, 4 pages.

* cited by examiner

MYOGRAM DETERMINATION FROM ECG SIGNAL

BACKGROUND

The present disclosure relates generally to the field of biological signal measurement. More particularly, the present disclosure relates to systems of and methods for measuring myographic signals from captured ECG signals.

Assessment of a patient's respiratory condition may be useful for a variety of purposes. For example, a patient's respiratory condition may be evaluated in clinical environments to confirm whether there is a risk to the patient's respiratory health or function. In some implementations, information regarding a patient's respiratory condition may be used in performing related operations, such as capturing an electrocardiogram (ECG) signal. For example, because respiratory-related muscle movements can cause body shifts (e.g., heart movements) that can affect captured ECG signals, respiratory-related information may be useful in ensuring that ECG signals are captured during periods of less respiratory movement. There is a need for a system that can extract muscle activity information, such as respiratory information, from ECG signals and is able to isolate the components of the muscle activity information associated with individual electrodes.

SUMMARY

One embodiment of the disclosure relates to a method of measuring signals representative of muscle activity. The method includes detecting, using a processing circuit, an electrocardiogram (ECG) signal through a plurality of electrodes. The ECG signal includes a plurality of ECG sample signals, and each ECG sample signal is a bipolar signal associated with two of the plurality of electrodes and includes a cardiac signal component and a myographic signal component representative of muscle contractions relating to the muscle activity. The method further includes filtering, using the processing circuit, each of the ECG sample signals to remove at least a portion of the cardiac signal component and generate a combined myographic power signal for the two of the plurality of electrodes with which the ECG sample signal is associated. Each combined myographic power signal represents a myographic potential between the two electrodes. The method further includes calculating, using the processing circuit, individual myographic power signals for each of the plurality of electrodes by applying the combined myographic power signals within a covariance matrix.

Another embodiment relates to a system for measuring signals representative of muscle activity. The system includes a circuit configured to detect an electrocardiogram (ECG) signal through a plurality of electrodes. The ECG signal includes a plurality of ECG sample signals, and each ECG sample signal is a bipolar signal associated with two of the plurality of electrodes and comprises a cardiac signal component and a myographic signal component representative of muscle contractions relating to the muscle activity. The circuit is further configured to filter each of the ECG sample signals to remove at least a portion of the cardiac signal component and generate a combined myographic power signal for the two of the plurality of electrodes with which the ECG sample signal is associated. Each combined myographic power signal represents a myographic potential between the two electrodes. The circuit is further configured to calculate individual myographic power signals for each of the plurality of electrodes by applying the combined myographic power signals within a covariance matrix.

Another embodiment relates to a system for measuring signals representative of respiratory activity. The system includes a plurality of electrodes configured to capture an electrocardiogram (ECG) signal. The ECG signal includes a plurality of ECG sample signals, and each ECG sample signal is a bipolar signal associated with two of the plurality of electrodes and comprises a cardiac signal component and a myographic signal component representative of muscle contractions relating to the respiratory activity. The system further includes a circuit operably coupled to the plurality of electrodes and including a microprocessor. The circuit is configured to designate one of the plurality of electrodes to be a reference electrode and the others of the plurality of electrodes to be recording electrodes. The circuit is further configured to detect a first set of ECG sample signals within the ECG signal. The first set of ECG sample signals comprises an ECG sample signal for each recording electrode with respect to the reference electrode. The circuit is further configured to filter each of the first set of ECG sample signals to remove at least a portion of the cardiac signal component and generate a first set of combined myographic power signals. The first set of combined myographic power signals comprises a combined myographic power signal for each recording electrode with respect to the reference electrode. The circuit is further configured to calculate an individual myographic power signal for the reference electrode by applying the first set of combined myographic power signals within a covariance matrix. The circuit is further configured to calculate individual myographic power signals for each of the plurality of electrodes other than the reference electrode by: (1) changing the reference electrode to another of the plurality of electrodes to designate a new reference electrode; (2) designating the electrodes of the plurality of electrodes other than the new reference electrode to be new recording electrodes; (3) determining a second set of combined myographic power signals including a combined myographic power signal for each new recording electrode with respect to the new reference electrode; (4) calculating the individual myographic power signal for the new reference electrode by applying the second set of combined myographic power signals within the covariance matrix; and (5) repeating the changing, designating, determining, and calculating operations until the individual myographic power signals have been calculated for each of the plurality of electrodes.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Figure 1:
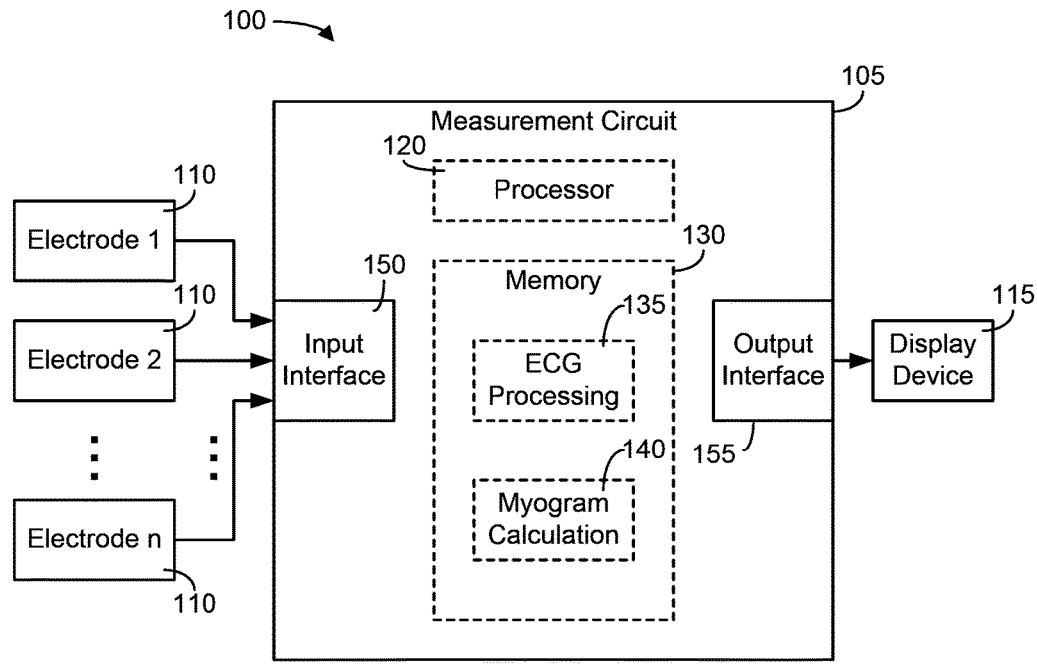
FIG. 1 is a block diagram of a system for measuring signals representative of respiratory activity according to an exemplary embodiment.

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

Referring generally to the figures, systems and methods that may be used to measure and/or calculate myographic signals representative of muscle activity (e.g., respiratory activity) from captured electrocardiogram (ECG) signals are provided according to exemplary embodiments. Systems configured to measure myographic signals representative of muscle contractions resulting from respiratory movements (e.g., movements of the diaphragm and/or intercostal muscles) often use separate devices dedicated to measuring respiratory function. For example, such systems may utilize air flow sensors, mechanical movement sensors, and/or other types of sensors to measure air flow and/or body movement resulting from respiratory activity. Such sensors may provide for effective measurement of respiratory function, but separate sensors result in added expense and complexity for the system to achieve respiratory monitoring.

Some ECG systems may be configured to monitor some respiratory activity by processing myographic signals from within captured ECG signals. Such systems may avoid the expense and complexity of utilizing dedicated sensors for measuring respiratory information. Such systems measure myographic data for a combination of electrodes. For example, the systems may measure bipolar myographic potentials between two electrodes. Such bipolar myographic potentials may represent a difference in myographic potentials between the two electrodes. Unless the two electrodes are very close together, the myographic potentials at each electrode are independent, and the myographic power calculated using the bipolar signals may be a combination (e.g., sum) of the myographic power signals occurring at each electrode. Thus, such systems cannot distinguish between the components of the combined myographic power signal attributable to each individual electrode.

The systems and methods of the present disclosure are configured to calculate myographic signals from ECG signals in a manner in which the myographic signals may be isolated to individual electrodes. An exemplary system may detect an ECG signal that includes several ECG sample signals sampled over a sampling timeframe. Each sample signal may be a bipolar signal associated with two electrodes, and may include a cardiac signal component and a myographic signal component representative of muscle contractions relating to respiratory activity. The system may filter the ECG sample signals to remove at least a portion of the cardiac signal components and generate combined (e.g., bipolar) myographic power signals. Each combined myographic power signal represents a myographic potential between two electrodes. In some embodiments, the filtering may include high pass filtering to remove large low frequency cardiac signal components of the ECG sample signals. In some embodiments, the filtering may additionally or alternatively be configured to remove at least a portion of the ECG sample signals at a frequency at or near 50 Hz and/or 60 Hz (e.g., remove alternating current (AC) interference).

The system may apply the combined myographic power signals resulting from the filtering in a covariance matrix, and may calculate individualized myographic power signals for each electrode using the covariance matrix. For example, in some embodiments, the system may initially designate one electrode as a reference electrode and the other electrodes as recording electrodes. Bipolar ECG sample signals may be collected by the system for each recording electrode with respect to the reference electrode. The bipolar ECG sample signals may be filtered to remove at least a portion of the cardiac components and generate bipolar myographic power signals. The system may then utilize a covariance matrix that includes the bipolar myographic power signals to calculate an individual myographic power signal associated with the reference electrode. For example, the individual myographic power signal for the reference electrode may be calculated based on one or more off-diagonal elements in the covariance matrix. The reference electrode then may be changed to another electrode, bipolar myographic power signals may be recalculated for the new recording electrodes with respect to the new reference electrode, and an individual myographic power signal may be calculated by applying the new bipolar myographic power signals within the covariance matrix. The system may repeat this process until an individual myographic power signal has been calculated for each electrode, or for all electrodes for which an individual myographic power estimate is desired.

Determining myographic power signals associated with individual electrodes may provide one or more of various advantages. For example, the location of electrodes is often determined by the exigencies of the ECG recording. If the only available myographic power estimates are from pairs of electrodes, it is likely that some members of the pairs have substantially different myographic power than their opposite member. The difference may be not only in the magnitude of the myographic power, but also in its nature. For example, an electrode on the arm or leg might record peripheral muscle activity unrelated to respiration, while an electrode on the chest will be more sensitive to intercostal muscle activity related to respiration. If only the combined/average myographic power is available, one type of activity may mask the other. In some embodiments, for example, capturing the myographic power from individual electrodes may permit the identification of optimized estimates of a particular activity such as respiration.

While the exemplary embodiments presented herein are described primarily with respect to muscle activity related to respiratory function, the systems and methods discussed herein may be utilized in detecting myographic signals relating to other types of muscle activity and/or for other purposed. For example, extracted myographic signals may be utilized to differentiate diaphragm-based breathing from chest/rib effort, depending on knowledge of the electrode placements. In another exemplary embodiment, the extracted myographic signal may be used to differentiate between leg and arm movements, where systems configured to determine a myographic signal associated with a combination of electrodes may only be able to determine that the myographic activity is associated with a combination of the leg and arm electrodes. In some embodiments, the extracted myographic signals may be used to optimize selection of ECG bipolar leads with reduced noise, which may yield more accurate amplitude and/or ECG landmark detection. All such embodiments are contemplated within the scope of the present disclosure.

Referring now to FIG. 1, a block diagram of a system 100 including a measurement circuit 105 configured to measure an ECG and calculate electrode-specific myographic signals is shown according to an exemplary embodiment. Circuit 105 may include a processor 120, which may be any general purpose or special purpose processor (e.g., FPGA, CPLD, ASIC, etc.). Circuit 105 may also include a memory 130, which may include any computer readable storage medium (e.g., RAM, ROM, PROM, hard disk, optical storage, flash storage, etc.).

Circuit 105 may be configured to detect ECG signals through two or more electrodes 110 configured to measure electrical signals through contact with the patient's skin. Electrodes 110 may be coupled to circuit 105 through an input interface 150, which may be any wired or wireless interface suitable for communicatively coupling electrodes 110 to circuit 105. Memory 130 may include an ECG processing module 135 (e.g., instructions configured to be executed by processor 120) configured to receive input signals from electrodes 110 and to perform processing to generate the ECG signal. In some embodiments, ECG processing module 135 may process the ECG signal into a textual and/or graphical format suitable for presentation to a user and transmit the resultant data to a display device 115 (e.g., any display device, such as a CRT, LCD, LED, etc.) via an output interface 155 (e.g., any wired and/or wireless interface, such as a USB interface, WiFi interface, Bluetooth interface, serial port, etc.). In some embodiments, ECG processing module 135 may process the ECG signal to identify one or more signal components within the signal, such as a P wave and/or QRS wave within the ECG signal.

Memory 130 may also include a myogram calculation module 140 configured to extract myographic components from the ECG signal and calculate a myographic signal for one or more of electrodes 110. The captured ECG signal may include both cardiac components related to the function of the heart and myographic components related to respiratory activity. For example, the myographic components may be electrical potentials generated by the diaphragm and intercostal muscles responsible for respiratory function. Myogram calculation module 140 may be configured to isolate the myographic components of the ECG signal and remove at least some of the cardiac components. Myogram calculation module 140 may then perform calculations on the remaining ECG signal components to determine myographic power signals associated with individual ones of electrodes 110. In some embodiments, myogram calculation module 140 may be configured to generate a textual and/or graphical representation of the individualized myographic power signals for each electrode 110 and transmit the information to display device 115 for presentation to a user.

Figure 2:
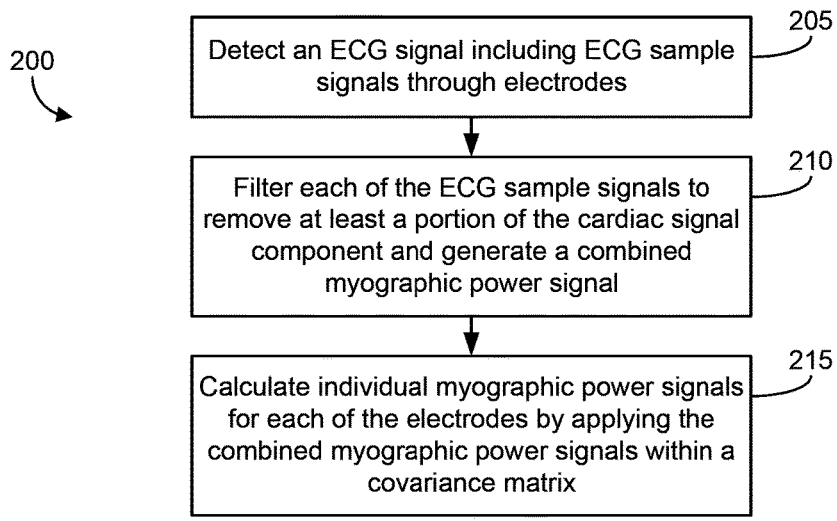
FIG. 2 is a flow diagram of a process calculating signals representative of respiratory activity according to an exemplary embodiment.

FIG. 2 illustrates a flow diagram of a process 200 for calculating individual myographic power signals from and ECG signal according to an exemplary embodiment. Referring now to both FIGS. 1 and 2, circuit 105 may be configured to detect the ECG signal using electrodes 110 (205). The ECG signal may include several ECG sample signals or sequences sampled at a particular sampling rate. The ECG sample signals may be bipolar signals, or relative signals representative of a measured difference (e.g., electrical potential difference) between two electrodes 110. Each ECG sample signal may include a cardiac component and a myographic component representative of muscle contractions relating to the respiratory activity.

Circuit 105 may be configured to filter each of the ECG sample signals to remove at least a portion of the cardiac signal component and/or emphasize a portion of the myographic component and generate a combined myographic power signal (210). The combined myographic power signal may represent a myographic potential between the two electrodes with which the combined myographic power signal is associated. A myogram is a wide spectrum, low amplitude signal often not visible in an ECG at normal amplification. The ECG signal has large low frequency components distributed largely throughout the sample sequence. Circuit 105 may be configured to focus on recovery of the high frequency components of the myogram and remove these large low frequency ECG signal components. For example, circuit 105 may remove the low frequency components using a high pass filter (e.g., a hardware and/or software signal filter). In some embodiments, circuit 105 may further filter the ECG sample signals to remove at least some remaining high frequency cardiac components. For example, circuit 105 may identify one or more high frequency components present in the ECG sample signals (e.g., one or more QRS waves and/or P waves) and replace components of the ECG sample signals at the location of the identified QRS and/or P waves with corresponding components from previous samples that did not include the QRS and/or P waves. In some embodiments, circuit 105 may additionally or alternatively filter the ECG sample signals to remove frequency components corresponding to frequencies of 50 Hz and/or 60 Hz (e.g., remove AC interference/noise). Once the filtering has been completed, circuit 105 may obtain the combined myographic power signal for each ECG sample signal.

Circuit 105 may be configured to calculate individual myographic power signals for each electrode 110 by applying the combined myographic power signals within a covariance matrix (215). Circuit 105 may be configured to compute one or more covariance matrix elements using the combined (e.g., bipolar) myographic power signals. In some implementations, circuit 105 may calculate individual myographic power signals for a particular electrode by designating that electrode as a reference, determining the combined myographic power signals for the other electrodes with respect to the reference electrode, and calculating the individual myographic power signal based on one or more off-diagonal elements of the covariance matrix.

Figure 3:
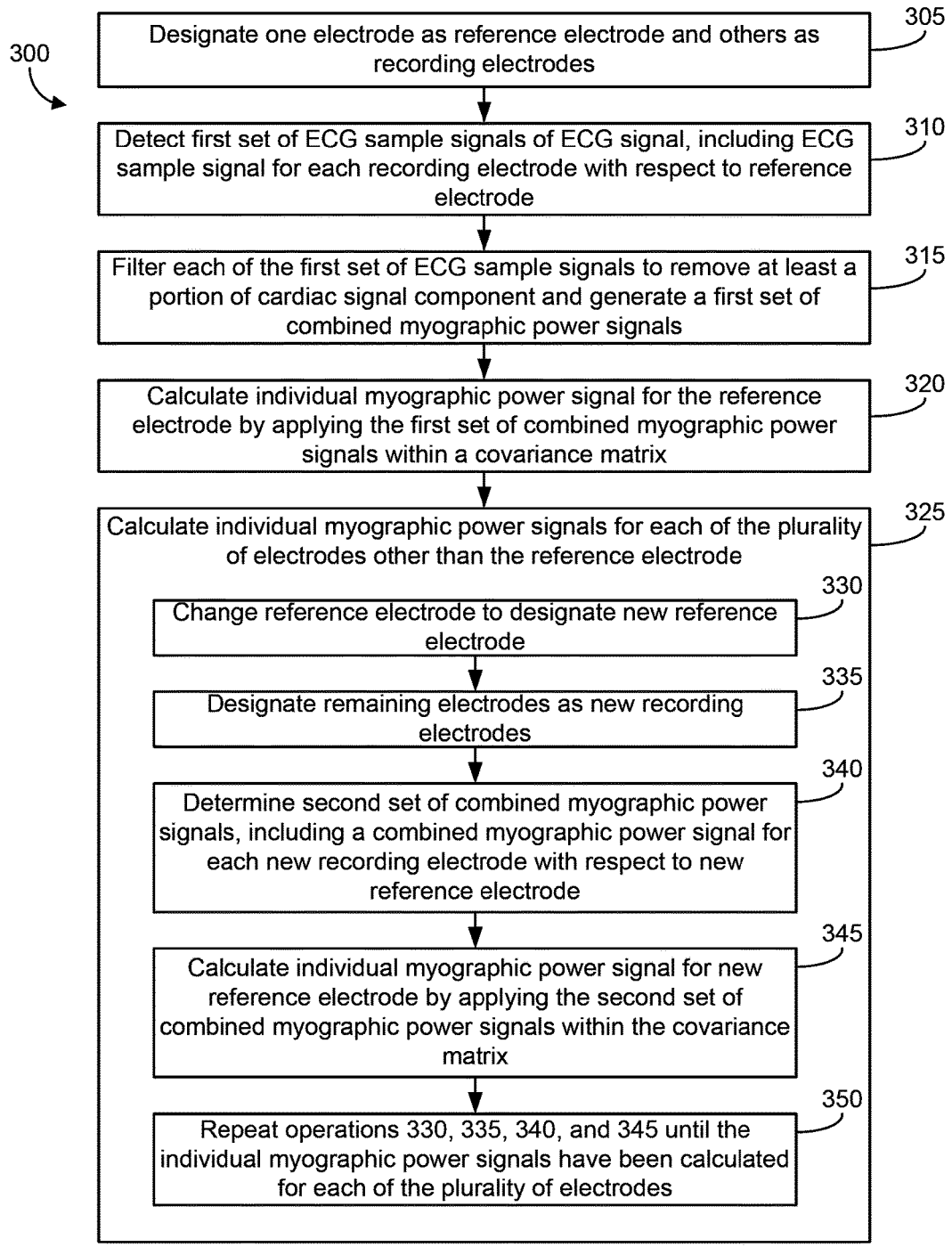
FIG. 3 is a flow diagram of a more detailed process for calculating signals representative of respiratory activity that are specific to individual electrodes to an exemplary embodiment.

FIG. 3 illustrates a more detailed flow diagram of a process 300 for calculating individual myographic power signals for different electrodes according to an exemplary embodiment. Referring to both FIGS. 1 and 3, circuit 105 may initially designate one of electrodes 110 as a reference electrode and the other electrodes 110 as recording electrodes (305). Circuit 105 may detect an ECG signal including a first set of ECG sample signals (310). The first set of ECG sample signals may include a sample sequence for each recording electrode with respect to the reference electrode. In some embodiments, a sample sequence y(i) may be obtained for each of the bipolar signals to be used in the covariance matrix calculation (e.g., for each recording electrode with respect to the reference electrode), wherein "i" designates a sample number. In some embodiments, each sample sequence y(i) may include a predetermined sample rate, such as 1000 samples/second. In one exemplary embodiment in which the system includes three electrodes C0, C1, and C2, where C0 is initially designated as the reference electrode, the ECG signal may include sample sequence $y_1(i)$ measured between recording electrode C1 and reference electrode C0, and sample sequence $y_2(i)$ measured between recording electrode C2 and reference electrode C0.

Circuit 105 may filter each of the first set of ECG sample signals to remove at least a portion of the cardiac components of the signals and generate a first set of combined (e.g., bipolar) myographic power signals (315). In some embodiments, circuit 105 may apply a low pass filter to the ECG sample signals to generate a low pass filtered sequence. One such low pass filter may be defined as follows:

$$ylow(i)=y(i)+y(i+1)+y(i+2)$$

The low pass filter may be applied to each bipolar sample signal to generate $ylow_1(i)$ and $ylow_2(i)$ low pass filtered signals for electrodes C1 and C2, respectively, with reference to reference electrode C0. In some embodiments, because the myographic signal may be very low in amplitude, the highest frequencies in a particular sequence (e.g., a 1000 s/s sequence) may have broad spectrum noise content from the acquisition signal that exceeds the myographic signal components (e.g., quantization noise from the analog-to-digital conversion process). In some such embodiments, low pass filtering may be used to discard frequencies above a particular level, such as 200 Hz.

The sample signals may additionally or alternatively be applied to a high pass filter configured to remove low frequency components of the ECG signal. One suitable high pass filter may be the third difference over 18 milliseconds, and may be represented by the following:

$$yhigh(i)=ylow(i)-3*ylow(i+6)+3*ylow(i+12)-ylow(i+18)$$

This filter provides a −18 dB/octave roll off of low frequencies with a −3 dB roll off at approximately 50 Hz. Such a filter is effective at removing most of the ECG cardiac signal components apart from high frequency components of the P and QRS waves. The high pass filter may be applied to generate high pass filtered sample signals for each recording electrode with respect to the reference electrode, $yhigh_1(i)$ and $yhigh_2(i)$.

The amplitudes of the remaining high frequency components of the ECG may readily exceed those of the myographic components. To account for this, circuit 105 may be configured to determine the location of the P and/or QRS waves within the filtered sample sequences. In some embodiments, the location of the P and/or QRS waves may be determined by ECG processing module 135 using a conventional method of detecting and identifying P and/or QRS waves within an ECG signal. If any of the samples y(i) included in the calculation of yhigh(i) are within a P wave and/or QRS wave of the ECG signal, the value of yhigh(i) may be replaced by a different sample. For example, yhigh(i) may be replaced by yhigh(i−100) (e.g., if the P wave and/or QRS wave is expected to have a duration under 100 milliseconds). In some circumstances yhigh(i−100) may have already been replaced by yhigh(i−200), and so on. In some embodiments, a different duration may be chosen, such as 200 milliseconds. The resultant filtered signal may be an estimation of the sample sequences without the presence of the P and/or QRS waves.

In some embodiments, the samples may be further filtered to reduced AC interference, such as frequency components at 50 Hz, 60 Hz, and/or their harmonics that may serve to mask the myographic signal components. Such a filter may define a further filtered sequence z(i)=yhigh(i)−yhigh(i−100) in cases where yhigh(i) has not been replaced due to overlapping P and/or QRS waves. When yhigh(i) has been replaced, the sequence may be defined as z(i)=z(i−100). This method may be used to calculate $z_1$ and $z_2$ for recording electrodes C1 and C2, respectively, with reference to reference electrode C0. In implementations in which myographic power is more desired than amplitude, circuit 105 may be configured to calculate the average value of the square of z(i) over an interval of time (e.g., 100 milliseconds).

Figure 4:
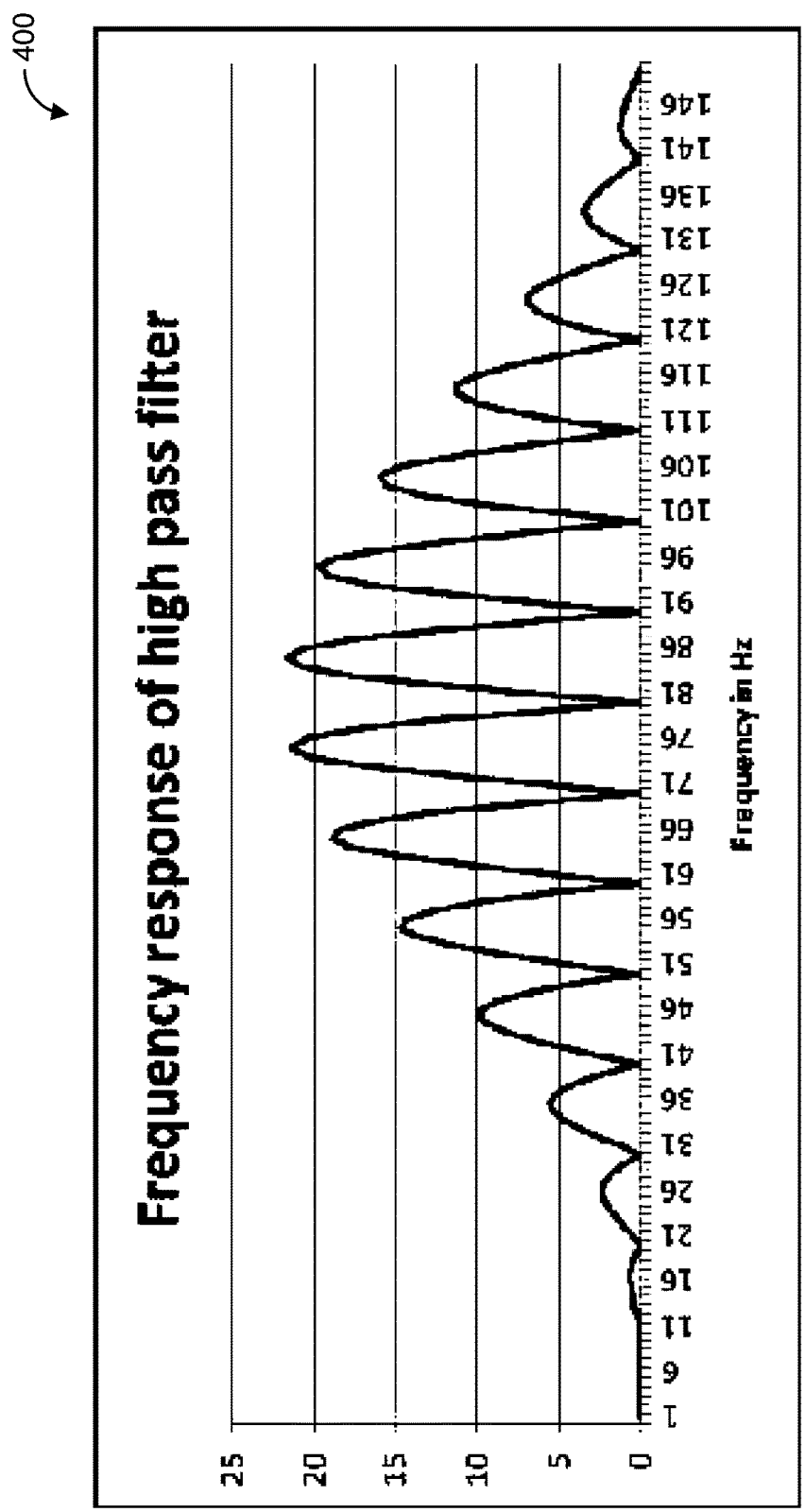
FIG. 4 is a graph of a frequency response for an illustrative high pass filter according to an exemplary embodiment.

FIG. 4 illustrates a graph 400 showing a frequency response of one illustrative filter to which sample sequences may be applied according to an exemplary embodiment. Graph 400 may correspond to the frequency response of filters yhigh(i) and/or z(i) discussed above. It can be seen in graph 400 that there is a null response at approximately 50 Hz and 60 Hz, which may be designed to prevent AC interference present in the raw sample sequence y(i) from being present as additive noise in the myographic signal represented by z(i).

Referring again to FIGS. 1 and 3, circuit 105 may calculate an individual myographic power signal for the reference electrode C0 by applying the first set of combined myographic power signals within a covariance matrix (320). The combined (e.g., bipolar) myographic potential $z_k$ for a particular electrode k may be represented as follows, where $e_k$ is the myographic potential associated with electrode k and $e_0$ is the myographic potential associated with reference electrode C0:

$$z_k(i)=e_k(i)-e_0(i)$$

A covariance matrix M[j,k] can be calculated for z(i), which may be defined as the average product of $z_j(i)*z_k(i)$ over a particular sampling period (e.g., 100 milliseconds, including 100 samples at a rate of 1000 samples/second). The covariance matrix M[j,k] may be calculated as follows:

$$M[j,k]=<z_j(i)*z_k(i)>$$

$$=<(e_j(i)-e_0(i))*(e_k(i)-e_0(i))>$$

$$=<e_j(i)*e_k(i)>-<e_j(i)*e_0(i)>-<e_k(i)*e_0(i)>+<e_0(i)*e_0(i)>$$

When j and k are not equal, corresponding to the off diagonal elements of the covariance matrix, the first three terms in the last equation above are each, on average, zero, based on the assumption that $e_k(i)$ contains only myographic potentials after the cardiac components have been filtered out of the ECG sample signals, and that the myographic potentials at different electrodes are uncorrelated. Under these assumptions, each of the off diagonal elements of the covariance matrix provides an estimate of the myographic power at electrode C0, $<e_0(i)*e_0(i)>$. The off diagonal elements may be averaged to provide an estimate of the myographic power associated with electrode C0. In some embodiments, a covariance matrix may be calculated for each of several sample sequence blocks (e.g., containing 100 samples, or 100 milliseconds), and the resultant values for different blocks may provide a sequence of myographic power values specific to electrode C0.

Figure 5:
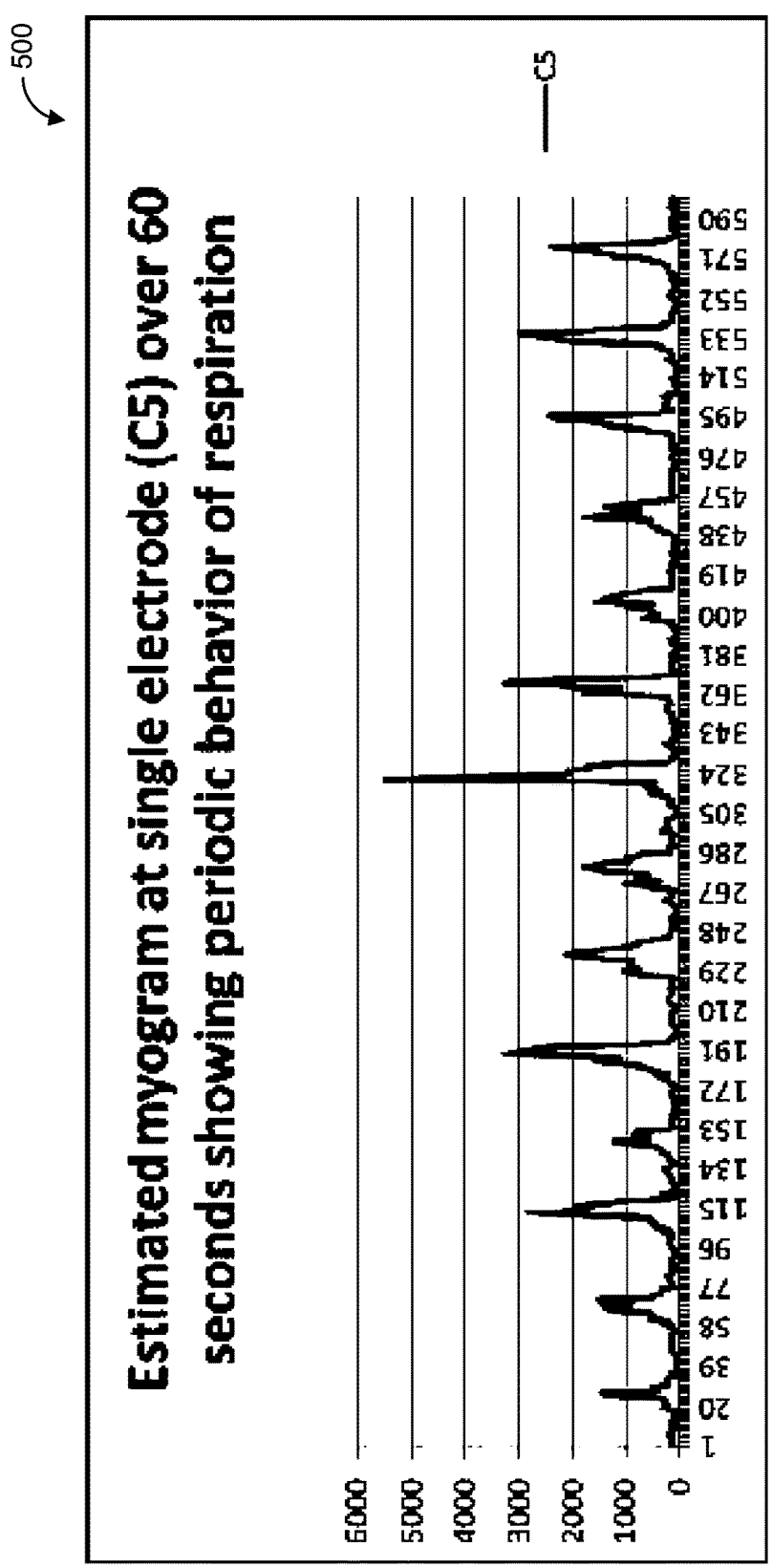
FIG. 5 is a graph of an estimated myographic signal for a particular electrode over a sampling time period according to an exemplary embodiment.

FIG. 5 illustrates a graph 500 showing an estimated myographic power signal associated with a single electrode over a period of 60 seconds according to an exemplary embodiment. Graph 500 illustrates the periodic behavior of the respiratory activity measured in the area near the single electrode.

Referring again to FIGS. 1 and 3, circuit 105 may be configured to calculate individual myographic power signals for each electrode 110 other than the current reference electrode (325). For example, in the three electrode system noted above, circuit 105 may be configured to calculate individual myographic power signals for electrodes C1 and C2 as well. Circuit 105 may be configured to change the reference electrode to designate a new reference electrode (330), such as electrode C1, and designate the remaining electrodes as new recording electrodes (335). Circuit 105 may then determine a second set of combined myographic power signals for the new recording electrodes C0 and C2 with respect to new reference electrode C1 (340). The second set of combined myographic power signals may be determined using the originally captured and processed combined myographic power signals. For example, to calculate the new sample sequences when the reference is changed from C0 to C1, the value of $z_1(i)=e_1(i)-e_0(i)$ may be subtracted from the original samples, which converts $$z_{2\text{-}original}(i)=e_2(i)-e_0(i)$$

to $$z_{2\text{-}new}(i)=e_2(i)-e_1(i).$$

The negated value of $z_1(i)$ may become the second bipolar myographic signal referenced to C1 (e.g., $z_{0\text{-}new}(i)=-z_{1\text{-}original}(i)$). The second set of combined myographic power signals with reference to new reference electrode C1 may be applied to one or more covariance matrices to determine an individual myographic power signal for electrode C1 in a manner similar to that noted above (345). Circuit 105 may repeat operations 330-345 until the individual myographic power signals have been calculated for each electrode 110 for which individual myographic power signals are desired (350).

While the discussion above focuses on an example including three electrodes, it should be appreciated that the methods described may be applied to a system with any number of electrodes. For example, if a system having four electrodes is used, additional off diagonal covariance matrix elements (e.g., elements M[1,2], M[1,3], and M[2,3]) may be calculated to estimate the individual myographic power signal at a particular electrode. In some implementations, the off diagonal elements may be combined (e.g., averaged) to generate the individualized estimates. In some embodiments, the additional off diagonal elements may be used to test the validity of the assumption that the myographic noise is uncorrelated between electrodes. If the assumption is valid, each of the off diagonal elements should be approximately equal.

The disclosure is described above with reference to drawings. These drawings illustrate certain details of specific embodiments that implement the systems and methods of the present disclosure. However, describing the disclosure with drawings should not be construed as imposing on the disclosure any limitations that may be present in the drawings. The present disclosure contemplates methods, systems and program products on any machine-readable media for accomplishing its operations. The embodiments of the present disclosure may be implemented using an existing computer processor, or by a special purpose computer processor incorporated for this or another purpose or by a hardwired system. No claim element herein is to be construed under the provisions of 35 U.S.C. §112, sixth paragraph, unless the element is expressly recited using the phrase "means for." Furthermore, no element, component or method step in the present disclosure is intended to be dedicated to the public, regardless of whether the element, component or method step is explicitly recited in the claims.

Embodiments within the scope of the present disclosure include program products comprising machine-readable storage media for carrying or having machine-executable instructions or data structures stored thereon. Such machine-readable storage media can be any available media which can be accessed by a general purpose or special purpose computer or other machine with a processor. By way of example, such machine-readable storage media can include RAM, ROM, EPROM, EEPROM, CD ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable storage media. Machine-executable instructions include, for example, instructions and data which cause a general purpose computer, special purpose computer, or special purpose processing machine to perform a certain function or group of functions. Machine or computer-readable storage media, as referenced herein, do not include transitory media (i.e., signals in space).

Embodiments of the disclosure are described in the general context of method steps which may be implemented in one embodiment by a program product including machine-executable instructions, such as program code, for example, in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

An exemplary system for implementing the overall system or portions of the disclosure might include a general purpose computing device in the form of a computer, including a processing unit, a system memory, and a system bus that couples various system components including the system memory to the processing unit. The system memory may include read only memory (ROM) and random access memory (RAM) or other storage medium. The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated machine-readable media provide nonvolatile storage of machine-executable instructions, data structures, program modules, and other data for the computer. A computer readable storage medium, as referenced herein, is tangible and non-transitory (i.e., does not include mere signals in space).

It should be noted that although the flowcharts provided herein show a specific order of method steps, it is understood that the order of these steps may differ from what is depicted. Also, two or more steps may be performed concurrently or with partial concurrence. Such variation will depend on the software and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps and decision steps. It should also be noted that the word "component" as used herein and in the claims is intended to encompass implementations using one or more lines of software code, and/or hardware implementations, and/or equipment for receiving manual inputs.

The foregoing description of embodiments of the disclosure have been presented for purposes of illustration and description. It is not intended to be exhaustive or to limit the disclosure to the precise form disclosed, and modifications and variations are possible in light of the above teachings or may be acquired from practice of the disclosure. The embodiments were chosen and described in order to explain the principals of the disclosure and its practical application to enable one skilled in the art to utilize the disclosure in various embodiments and with various modifications as are suited to the particular use contemplated.

What is claimed is:

1. A method of measuring signals representative of muscle activity, the method comprising:
   detecting, using a processing circuit, an electrocardiogram (ECG) signal through a plurality of electrodes, wherein the ECG signal comprises a plurality of ECG sample signals, wherein each ECG sample signal is a bipolar signal associated with two of the plurality of electrodes and comprises a cardiac signal component and a myographic signal component representative of muscle contractions relating to the muscle activity;
   filtering, using the processing circuit, each of the ECG sample signals to remove at least a portion of the cardiac signal component and generate a combined myographic power signal for the two of the plurality of electrodes with which the ECG sample signal is associated, wherein each combined myographic power signal represents a myographic potential between the two electrodes; and
   calculating, using the processing circuit, individual myographic power signals for each of the plurality of electrodes by applying the combined myographic power signals within a covariance matrix;
   wherein:
      the method further comprises designating one of the plurality of electrodes to be a reference electrode and the others of the plurality of electrodes to be recording electrodes;
      detecting the ECG signal comprises detecting a first set of ECG sample signals comprising an ECG sample signal for each recording electrode with respect to the reference electrode;
      filtering each of the ECG sample signals comprises filtering each of the first set of ECG sample signals to generate a first set of combined myographic power signals, wherein the first set of combined myographic power signals comprises a combined myographic power signal for each recording electrode with respect to the reference electrode; and
      calculating the individual myographic power signals comprises applying the first set of combined myographic power signals within the covariance matrix and calculating the individual myographic power signal for the reference electrode.

2. The method of claim 1, wherein the individual myographic power signal for the reference electrode is calculated based on one or more off-diagonal combined myographic power signals within the covariance matrix.

3. The method of claim 1, further comprising:
   changing the reference electrode to another of the plurality of electrodes to designate a new reference electrode;
   designating the electrodes of the plurality of electrodes other than the new reference electrode to be new recording electrodes;
   determining a second set of combined myographic power signals comprising a combined myographic power signal for each new recording electrode with respect to the new reference electrode; and
   calculating the individual myographic power signal for the new reference electrode by applying the second set of combined myographic power signals within the covariance matrix.

4. The method of claim 3, further comprising repeating the changing, designating, determining, and calculating operations until the individual myographic power signals have been calculated for each of the plurality of electrodes.

5. The method of claim 1, wherein filtering each of the ECG sample signals to generate a combined myographic power signal for the two of the plurality of electrodes with which the ECG sample signal is associated comprises applying a high pass filter to the ECG sample signals to remove low frequency components of the ECG sample signals.

6. The method of claim 5, wherein filtering each of the ECG sample signals to generate a combined myographic power signal for the two of the plurality of electrodes with which the ECG sample signal is associated further comprises:
   determining a presence of at least one of a QRS wave or a P wave within a portion of the ECG sample signals; and
   replacing the portion of the ECG sample signals including the at least one of the QRS wave or the P wave with a corresponding portion of the ECG sample signals from a previously detected sample.

7. The method of claim 5, wherein filtering each of the ECG sample signals to generate a combined myographic power signal for the two of the plurality of electrodes with which the ECG sample signal is associated further comprises filtering out at least a portion of the ECG sample signals corresponding to a frequency of at least one of 50 Hz or 60 Hz.

8. A system for measuring signals representative of muscle activity, the system comprising:
   a circuit configured to:
      detect an electrocardiogram (ECG) signal through a plurality of electrodes, wherein the ECG signal comprises a plurality of ECG sample signals, wherein each ECG sample signal is a bipolar signal associated with two of the plurality of electrodes and comprises a cardiac signal component and a myographic signal component representative of muscle contractions relating to the muscle activity;
      filter each of the ECG sample signals to remove at least a portion of the cardiac signal component and generate a combined myographic power signal for the two of the plurality of electrodes with which the ECG sample signal is associated, wherein each combined myographic power signal represents a myographic potential between the two electrodes; and
      calculate individual myographic power signals for each of the plurality of electrodes by applying the combined myographic power signals within a covariance matrix;
   wherein the circuit is configured to:
      designate one of the plurality of electrodes to be a reference electrode and the others of the plurality of electrodes to be recording electrodes;
      detect a first set of ECG sample signals comprising an ECG sample signal for each recording electrode with respect to the reference electrode;
      filter each of the first set of ECG sample signals to generate a first set of combined myographic power signals, wherein the first set of combined myographic power signals comprises a combined myographic power signal for each recording electrode with respect to the reference electrode; and apply the first set of combined myographic power signals within the covariance matrix and calculate the individual myographic power signal for the reference electrode.

9. The system of claim 8, wherein the individual myographic power signal for the reference electrode is calculated based on one or more off-diagonal combined myographic power signals within the covariance matrix.

10. The system of claim 8, wherein the circuit is configured to:

change the reference electrode to another of the plurality of electrodes to designate a new reference electrode;

designate the electrodes of the plurality of electrodes other than the new reference electrode to be new recording electrodes;

determine a second set of combined myographic power signals comprising a combined myographic power signal for each new recording electrode with respect to the new reference electrode; and calculate the individual myographic power signal for the new reference electrode by applying the second set of combined myographic power signals within the covariance matrix.

11. The system of claim 10, wherein the circuit is configured to repeat the changing, designating, determining, and calculating operations until the individual myographic power signals have been calculated for each of the plurality of electrodes.

12. The system of claim 8, wherein the circuit is configured to apply a high pass filter to the ECG sample signals to remove low frequency components of the ECG sample signals.

13. The system of claim 12, wherein the circuit is configured to:

determine a presence of at least one of a QRS wave or a P wave within a portion of the ECG sample signals; and replace the portion of the ECG sample signals including the at least one of the QRS wave or the P wave with a corresponding portion of the ECG sample signals from a previously detected sample.

14. The system of claim 12, wherein the circuit is configured to filter out at least a portion of the ECG sample signals corresponding to a frequency of at least one of 50 Hz or 60 Hz.

* * * * *